United States Patent
Terada

(10) Patent No.: US 7,244,697 B2
(45) Date of Patent: Jul. 17, 2007

(54) DETERGENT COMPOSITION COMPRISING A SILICON DERIVATIVE HAVING A GROUP CONTAINING BOTH A HYDROXY GROUP AND A NITROGEN ATOM

(75) Inventor: Eiji Terada, Tokyo (JP)

(73) Assignee: Kao Corporation, Tokyo (JP)

( * ) Notice: Subject to any disclaimer, the term of this patent is extended or adjusted under 35 U.S.C. 154(b) by 150 days.

(21) Appl. No.: 10/522,616

(22) PCT Filed: Aug. 8, 2003

(86) PCT No.: PCT/JP03/10138

§ 371 (c)(1),
(2), (4) Date: Jan. 31, 2005

(87) PCT Pub. No.: WO2004/014326

PCT Pub. Date: Feb. 19, 2004

(65) Prior Publication Data

US 2006/0052273 A1    Mar. 9, 2006

(30) Foreign Application Priority Data

Aug. 9, 2002 (JP) ............................. 2002-232732

(51) Int. Cl.
 *C11D 9/36* (2006.01)
 *C11D 3/37* (2006.01)
 *C11D 1/02* (2006.01)
(52) U.S. Cl. ...................... 510/122; 510/119; 510/125; 510/466; 510/475; 510/476; 510/477; 510/434; 510/426

(58) Field of Classification Search ................ 510/119, 510/122, 125, 466, 475, 476, 477, 434, 426
See application file for complete search history.

(56) References Cited

U.S. PATENT DOCUMENTS

| 4,915,938 | A | * | 4/1990 | Zawadzki | ............... | 424/70.122 |
| 5,154,849 | A | * | 10/1992 | Visscher et al. | ............ | 510/150 |
| 5,807,956 | A | | 9/1998 | Czech | | |
| 6,923,954 | B2 | * | 8/2005 | Doi et al. | ................ | 424/70.19 |
| 2004/0115155 | A1 | * | 6/2004 | Salvador et al. | ......... | 424/70.13 |

FOREIGN PATENT DOCUMENTS

| EP | 0 399 706 | 11/1990 |
| EP | 0 803 527 | 10/1997 |
| WO | 99 29286 | 6/1999 |
| WO | 02 083759 | 10/2002 |
| WO | 03 066007 | 8/2003 |

* cited by examiner

*Primary Examiner*—Charles I. Boyer
(74) *Attorney, Agent, or Firm*—Oblon, Spivak, McClelland, Maier & Neustadt, P.C.

(57) ABSTRACT

AbtractProvided is a detergent composition comprising the following components (a), (b) and (c): (a) an anionic surfactant, (b) a water soluble cationized polymer having a weight average molecular weight of from 100,000 to 2,000,000 and a charge density of from 0.6 to 4 meq/g, and (c) a silicone derivative having a group containing both a hydroxy group and a nitrogen atom as a side chain thereof bonded to a silicon atom. The detergent composition provides rich foaming during washing and at the same time and is capable of giving excellent conditioning effects to the hair and the like.1 1.

8 Claims, No Drawings

DETERGENT COMPOSITION COMPRISING A SILICON DERIVATIVE HAVING A GROUP CONTAINING BOTH A HYDROXY GROUP AND A NITROGEN ATOM

FIELD OF THE INVENTION

The present invention relates to silicone-containing detergent compositions which provide advantages such as rich foaming during washing, excellent conditioning effects to the hair and the like, and are particularly useful as a shampoo.

BACKGROUND OF THE INVENTION

Although a water soluble cationized polymer has been used in hair detergents for the purpose of giving conditioning effects to the hair, it does not provide a satisfactory effect. Amino-modified silicones have been used as another material for giving excellent conditioning effects to the hair, but they do not exhibit their function sufficiently in hair detergents.

SUMMARY OF THE INVENTION

According to the present invention, there is thus provided a detergent composition comprising the following components (a), (b) and (c):

(a) an anionic surfactant, (b) a water soluble cationized polymer having a weight average molecular weight of from 100,000 to 2,000,000 and a charge density of from 0.6 to 4 meq/g, and (c) a silicone derivative having a group containing both a hydroxy group and a nitrogen atom as a side chain thereof bonded to a silicon atom.

DETAILED DESCRIPTION OF THE INVENTION

All references cited are hereby incorporated by reference.

The present invention relates to a detergent composition providing good foaming during washing and capable of giving excellent conditioning effects to the hair and the like.

The present inventors have found that a detergent composition satisfying the above-described demand is available by using, in combination, an anionic surfactant, a water soluble cationized polymer having a specific molecular weight and charge density, and a silicone derivative having a side chain containing both a hydroxy group and a nitrogen atom.

As the anionic surfactant of Component (a), sulfate-, sulfonate- and carboxylate-type surfactants are preferred. Specific examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkylphenyl ether sulfates, and higher fatty acid salts. Of these, polyoxyalkylene alkyl ether sulfates and alkyl sulfates are preferred, with those represented by the following formula (a1) or (a2) being particularly preferred.

$$RO(CH_2CH_2O)_nSO_3M \quad (a1)$$

$$R'OSO_3M \quad (a2)$$

wherein, R represents a $C_{10\text{-}18}$ alkyl or alkenyl group, R' represents a $C_{10\text{-}18}$ alkyl group, M represents an alkali metal, alkaline earth metal, ammonium, alkanolamine or basic amino acid, and n stands for a number of from 1 to 5 on weight average.

As Component (a), two or more of the above-described surfactants may be used in combination. The content of Component (a) in the detergent composition of the present invention preferably ranges from 0.5 to 60 wt. %, more preferably from 1 to 30 wt. %, especially preferably from 8 to 20 wt. % from the viewpoints of foaming performance, liquid state upon use and detergency.

The water soluble cationized polymer as Component (b) has a weight average molecular weight of from 100,000 to 2,000,000 and has a charge density of from 0.6 to 4 meq/g. When smoothness during foaming or rinsing is taken into consideration, the weight average molecular weight preferably ranges from 300,000 to 1,800,000, more preferably from 500,000 to 1,500,000, especially preferably from 700,000 to 1,200,000, while the charge density preferably ranges from 0.6 to 3 meq/g, especially preferably 0.7 to 2 meq/g.

Specific examples of the water soluble cationized polymer include cationized cellulose derivatives, cationic starch, cationized guar gum derivatives, homopolymers of diallyl quaternary ammonium salts, diallyl quaternary ammonium salt/acrylamide copolymers, quaternized polyvinylpyrrolidone derivatives, polyglycol polyamine condensates, vinylimidazolium trichloride/vinylpyrrolidone copolymers, hydroxyethyl cellulose/dimethyldiallylammonium chloride copolymers, vinylpyrrolidone/quaternized dimethylaminoethyl methacrylate copolymers, polyvinylpyrrolidone/alkylamino acrylate copolymers, polyvinylpyrrolidone/alkylamino acrylate/vinylcaprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, adipic acid/dimethylaminohydroxypropyl ethylenetriamine copolymer ("Cartaretin", product of Sandoz/USA), and cationic polymers as described in Japanese Patent Laid-Open Nos. 139734/1978 and 36407/1985. Among these, cationized cellulose derivatives and cationized guar gum derivatives are particularly preferred.

Examples of the water soluble cationized polymer capable of satisfying the above-described requirements as to both the molecular weight and charge density include "Merquat 550" (a copolymer of acrylamide and diallyl dimethyl ammonium salt; CTFA name: Polyquaternium-7; product of ONDEO-NALCO), "Luviquat FC370" (a copolymer of 1-vinyl-2-pyrrolidone and 1-vinyl-3-methylimidazolium salt; CTFA name: polyquaternium-16; product of BASF), "Gafquat 755N" (a copolymer of 1-vinyl-2-pyrrolidone and dimethylaminoethyl methacrylate; CTFA name: polyquaternium-11; product of ISP), "Polymer JR series" and "Polymer LR series" (salt of a reaction product between trimethyl ammonium substituted epoxide and hydroxyethyl cellulose; CTFA name: polyquaternium-10; product of Amerchol), and "Jaguar series" (guar hydroxypropyl trimonium chloride; product of Rhodia).

As Component (b), two or more of the water soluble cationized polymers as described above may be used in combination. From the viewpoint of the lubrication of foams and smoothness during the period of time from shampooing to rinsing, its content in the detergent composition of the present invention preferably ranges from 0.01 to 3 wt. %, more preferably from 0.05 to 2 wt. %, especially preferably from 0.1 to 1 wt. %.

The silicone derivative as Component (c) has a group containing both a hydroxy group and a nitrogen atom as a side chain bonded to a silicon atom. Preferred specific examples include those represented by the following average formula (1):

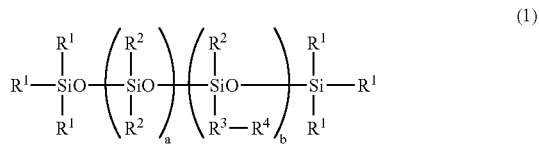

wherein, $R^1$s each independently represents a monovalent hydrocarbon group, a hydroxy group or an alkoxy group, $R^2$ each independently represents a monovalent hydrocarbon group, $R^3$ each independently represents a divalent $C_{1-10}$ hydrocarbon group, $R^4$ each independently represents a group represented by the following formula (2) or (3):

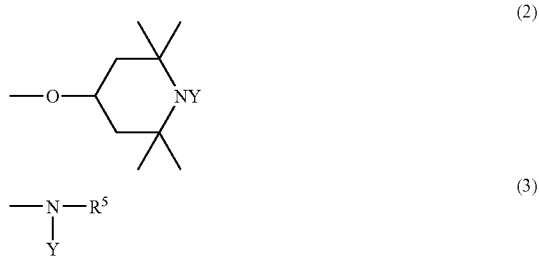

wherein, Y each independently represents a hydrogen atom or a group: $—CH_2CH(OH)—R^3—OH$ ($R^3$ has the same meaning as described above), $R^5$ each independently represents a hydrogen atom or a group $—R^3NY_2$ (Y and $R^3$ have the same meanings as described above), with the proviso that all the Ys do not represent a hydrogen atom simultaneously, a stands for a number of from 25 to 1,000, and b stands for a number of from 1 to 200.

Examples of the monovalent hydrocarbon group as R include alkyl groups and aryl groups. As $R^1$, $C_{1-3}$ alkyl groups (particularly, methyl group) and $C_{1-15}$, especially $C_{10-15}$, alkoxy groups are preferred.

Examples of the monovalent hydrocarbon group as $R^2$ include $C_{1-6}$ alkyl groups such as methyl, ethyl, propyl, butyl, pentyl and hexyl groups, $C_{6-10}$ aryl groups such as phenyl, tolyl and xylyl groups, and $C_{6-10}$ aralkyl groups such as benzyl and phenethyl groups. Among these, alkyl groups, especially a methyl group is preferred.

Examples of the divalent $C_{1-10}$ hydrocarbon group as $R^3$ include methylene group, alkylene groups such as ethylene, trimethylene, propylene, tetramethylene, methyltrimethylene, ethylethylene and dimethylethylene groups, and alkylene-arylene groups such as a group represented by the formula: $—(CH_2)_2—C_6H_4—$. Among these, $C_{2-4}$ alkylene groups are preferred.

When Y represents a group: $—CH_2CH(OH)—R^3—OH$, it is preferably a 2,3-dihydroxypropyl group. As $R^4$, groups represented by the formula (3) are preferred, while as $R^5$, N-(2,3-dihydroxypropyl)aminoethyl and N,N-bis(2,3-dihydroxypropyl)aminoethyl groups are preferred.

It is preferred that a stands for a number of from 75 to 400 and b stands for a number of from 1 to 20.

The silicone derivative serving as Component (c) can be synthesized, for example, by reacting an amino-modified silicone with an epoxy functional compound such as glycidol as described in EP-399706A2. Examples of the silicone derivative as Component (c) include compounds represented by the below-described formula, while those of commercially available products include "8500 Conditioning Agent" (CAS No. 237753-63-8; product of Dow Corning Corp).

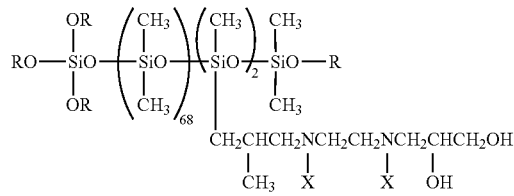

R: $C_{13}H_{27}$ to $C_{15}H_{31}$

X: 75% of $—CH_2CH(OH)CH_2OH$ and 25% of hydrogen atom

As Component (c), two or more of the silicone derivatives as described above may be used in combination. From the viewpoints of smoothness and softness of the hair during the period of time from shampooing to rinsing, and smoothness after drying, the content of Component (c) in the detergent composition of the present invention preferably ranges from 0.05 to 4 wt. %, more preferably from 0.07 to 2 wt. %, especially preferably from 0.1 to 1.5 wt. %.

The weight ratio of Component (b) to Component (c), that is, (b)/(c), is preferably from 1/10 to 10, especially preferably from 1/5 to 5 from the viewpoints of smoothness and softness of the hair during the period of time from shampooing to rinsing, and smoothness of the hair after drying.

To the detergent composition of the present invention, a nonionic surfactant or amphoteric surfactant may be added in order to improve foaming performance.

Examples of the nonionic surfactant include polyoxyalkylene sorbitan fatty acid esters, polyoxyalkylene sorbit fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglycerin alkyl ethers, polyglycerin fatty acid esters, fatty acid alkanolamides and alkyl glycosides. Among these, alkyl glycosides, polyoxyalkylene alkyl ethers, polyoxyalkylene ($C_8$ to $C_{20}$) fatty acid esters, polyoxyethylene sorbitan fatty acid esters, polyoxyethylene hydrogenated castor oils, and fatty acid alkanolamides are preferred. As fatty acid alkanolamides, those having a $C_{8-18}$, especially $C_{10-16}$ acyl group are preferred. The fatty acid alkanolamides may be either monoalkanolamides or dialkanolamides, and those having a $C_{2-3}$ hydroxyalkyl group are preferred. Examples include oleic diethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric isopropanolamide and lauric monoethanolamide.

As the amphoteric surfactant, betaine surfactants are usable. Among these, alkyldimethylaminoacetic betaines and fatty acid amidopropyl betaines are more preferred, with fatty acid amidopropyl betaines being particularly preferred. The fatty acid amidopropyl betaines preferably have a $C_{8-18}$, especially $C_{10-16}$ acyl group. Among these, lauramidopropyl betaine, palm kernel amidopropyl betaine and cocamidopropyl betaine are especially preferred.

To the detergent composition of the present invention, a conditioning component selected from cationic surfactants, silicones other than Component (c) and oils can be added in order to improve the finish after drying.

Examples of the cationic surfactant include lauryl trimethyl ammonium chloride, cetyl trimethyl ammonium chloride, cetyl trimethyl ammonium bromide, stearyl trimethyl ammonium chloride, stearyl trimethyl ammonium bromide, lauryl trimethyl ammonium bromide, behenyl trimethyl ammonium chloride, dialkyl dimethyl ammonium chloride, dicetyl dimethyl ammonium chloride, distearyl dimethyl ammonium chloride, dicocoyl dimethyl ammonium chloride, myristyl dimethyl benzyl ammonium chloride, stearyl dimethyl benzyl ammonium chloride, lanolin fatty acid amidopropyl ethyldimethyl ammonium ethyl sulfate, lanolin fatty acid amidoethyl triethyl ammonium ethyl sulfate, stearyl amidopropyl dimethylamine (and salts thereof), stearyl amidoethyl diethylamine (and salts thereof), stearoxy propyl dimethylamine (and salts thereof), stearoxy propyl trimethyl ammonium chloride, lanolin fatty acid amidopropyl triethyl ammonium ethyl sulfate, lanolin fatty acid amidoethyl trimethyl ammonium methyl sulfate, lanolin fatty acid amidopropyl ethyldimethyl ammonium methyl sulfate, isoalkanoic acid ($C_{14-20}$) amidopropyl ethyldimethyl ammonium ethyl sulfate, isoalkanoic acid ($C_{18-22}$) amidopropyl ethyldimethyl ammonium ethyl sulfate, isostearic acid amidopropyl ethyldimethyl ammonium ethyl sulfate, isononanoic acid amidopropyl ethyldimethyl ammonium ethyl sulfate and alkyl trimethyl ammonium saccharine.

As the silicones other than Component (c), the following compounds can be given as examples.

(Silicones-1) Dimethylpolysiloxane

Examples include compounds represented by the following formula:

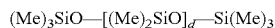

$(Me)_3SiO\text{—}[(Me)_2SiO]_d\text{—}Si(Me)_3$ wherein, Me represents a methyl group and d stands for a number of from 3 to 2,000.

(Sililcones-2) Amino-modified Silicone

Various amino-modified silicones are usable, but those having an average molecular weight of from about 3,000 to 100,000 and described under the name of Amodimethicone in the CTFA Dictionary (Cosmetic Ingredient Dictionary, USA), third edition are particularly preferred. This amino-modified silicone is preferably employed in the form of an aqueous emulsion and "SM 8704C" (product of Dow Corning Toray Silicone), "DC 929" (product of Dow Corning), etc. are the commercially available products of the aqueous emulsion.

(Silicones-3) The Other Silicones

In addition to the above-described silicones, usable are polyether-modified silicones, methylphenyl polysiloxane, fatty acid-modified silicones, alcohol-modified silicones, alkoxy-modified silicones, epoxy-modified silicones, fluorine-modified silicones, cyclic silicones, and alkyl-modified silicones.

The term "oils" to be used herein as the conditioning component means an oily substance other than silicones and examples include hydrocarbons such as squalene, squalane, liquid paraffin, liquid isoparaffin and cycloparaffin; glycerides such as castor oil, cacao oil, mink oil, avocado oil and olive oil; waxes such as beeswax, spermaceti, lanolin and carnauba wax; alcohols such as cetyl alcohol, oleyl alcohol, stearyl alcohol, isostearyl alcohol, 2-octyldodecanol and glycerin; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut fatty acid, isostearic acid and isopalmitic acid; and isostearyl glyceryl ether and polyoxypropylene butyl ether. Among these, esters, particularly hexadecyl 2-ethylhexanoate, isononyl isononanoate and isopropyl palmitate are preferred.

As the conditioning component, two or more of these compounds may be used in combination. Its content in the detergent composition of the invention preferably ranges from 0.05 to 10 wt. %, more preferably from 0.07 to 5 wt. %, especially preferably from 0.1 to 2 wt. % from the viewpoints of lubrication of foams, and smoothness during the period of time from shampooing to rinsing.

In addition to the above-described components, components conventionally used for a hair detergent can be incorporated in the detergent composition of the present invention, depending on the purpose. Such optional components include antidandruff, vitamins, bactericides, anti-inflammatory agents, antiseptics, chelating agents, humectants such as sorbitol and pantenol, colorants such as dyes and pigments, viscosity regulators such as hydroxyethyl cellulose, methyl cellulose, polyethylene glycol and clay minerals; pH regulators such as citric acid and potassium hydroxide; vegetable extracts; pearling agents; perfumes; coloring matters; ultraviolet absorbers; antioxidants; and the other components as described in the ENCYCLOPEDIA OF SHAMPOO INGREDIENTS (MICELLE PRESS).

Although the form of the detergent composition of the invention can be selected as needed from liquid, powder, gel and granule, a liquid type using water or a lower alcohol, particularly water as a solvent is preferred.

The detergent composition of the invention is preferably used as a hair shampoo composition or a body shampoo composition, of which a hair shampoo composition is preferred.

The detergent composition of the present invention preferably has a pH at 25° C. of from 3 to 10, especially from 3 to 7 when diluted 20 times the weight with water.

EXAMPLES

The following examples further describe and demonstrate embodiments of the present invention. The examples are given solely for the purpose of illustration and are not to be construed as limitations of the present invention.

Examples 1 to 4 and Comparative Examples 1 to 6

Shampoo compositions as shown in Table 1 were prepared and were organoleptically evaluated.

(Hair Washing Method)

After the hair was moistened sufficiently, 5 g or 10 g (5 g for medium-length hair and 10 g for long hair) of the shampoo composition was applied to the hair and the hair was washed therewith. The hair was then rinsed well with water, followed by sufficient drying with hot air from a dryer.

(Organoleptic Evaluation)

The shampoo compositions were evaluated by a panel of 10 experts based on the criteria described below and ranked based on the average score.

Evaluation Criteria (1) Smoothness of the Hair During Foaming and Rinsing and After Drying.
- 4: Very smooth
- 3: Smooth
- 2: Slightly smooth
- 1: Not so smooth
- 0: Not smooth (2) Softness of the Hair During Foaming
- 4: Very soft
- 3: Soft
- 2: Slightly soft
- 1: Not so soft
- 1: Rigid Rank

- A: an average score of not less than 3.5
- B: an average score of not less than 2.5 but less than 3.5
- C: an average score of not less than 1.5 but less than 2.5
- D: an average score less than 1.5

TABLE 1

|  | Composition (wt. %) | Examples | | | | Comparative Examples | | | | | |
|---|---|---|---|---|---|---|---|---|---|---|---|
|  |  | 1 | 2 | 3 | 4 | 1 | 2 | 3 | 4 | 5 | 6 |
| (a) | Sodium polyoxyethylene (2) lauryl ether sulfate | 10.0 | 10.0 | 10:0 | 10.0 | 10.0 | 10.0 | 10.0 | 10.0 | 10.0 | 10.0 |
| (b) | Cationized cellulose ("UCare Polymer JR-30M, product of Amerchol) $M_w$: 900000, charge density: 1.2 meq/g | 0.5 | — | — | — | 0.5 | — | — | — | — | 0.5 |
|  | Cationized cellulose ("UCare Polymer JR-400, product of Amerchol) $M_w$: 400000, charge density: 1.2 meq/g | — | 0.5 | — | — | — | 0.5 | — | — | — | — |
|  | Cationized guar gum ("Jaguar C-13S, product of RHODIA) $M_w$: 300000, charge density: 1.4 meq/g | — | — | 0.5 | — | — | — | 0.5 | — | — | — |
|  | Diallyl dimethyl ammonium chloride/acrylamide copolymer ("Merquat 550", product of ONDEO-NALCO) $M_w$: 1600000, charge density: 3.1 meq/g | — | — | — | 0.5 | — | — | — | 0.5 | — | — |
| (c) | Silicone derivative * | 0.5 | 0.5 | 0.5 | 0.5 | — | — | — | — | 0.5 | — |
| Others | Amino-modified silicone ("KT1989", product of GE Toshiba Silicone) | — | — | — | — | — | — | — | — | — | 0.5 |
|  | Cocamidopropyl betaine | 3.0 | 3.0 | 3.0 | 3.0 | 3.0 | 3.0 | 3.0 | 3.0 | 3.0 | 3.0 |
|  | Cocamide MEA | 1.0 | 1.0 | 1.0 | 1.0 | 1.0 | 1.0 | 1.0 | 1.0 | 1.0 | 1.0 |
|  | Ethylene glycol distearyl ester | 1.0 | 1.0 | 1.0 | 1.0 | 1.0 | 1.0 | 1.0 | 1.0 | 1.0 | 1.0 |
|  | Sodium chloride | 0.5 | 0.5 | 0.5 | 0.5 | 0.5 | 0.5 | 0.5 | 0.5 | 0.5 | 0.5 |
|  | Perfume | trace | trace | trace | trace | trace | trace | trace | trace | trace | trace |
|  | Citric acid | q.s. | q.s. | q.s. | q.s. | q.s. | q.s. | q.s. | q.s. | q.s. | q.s. |
|  | Purified water | balance | balance | balance | balance | balance | balance | balance | balance | balance | balance |
| pH (diluted to 20 times the weight with water) | | 6.0 | 6.0 | 6.0 | 6.0 | 6.0 | 6.0 | 6.0 | 6.0 | 6.0 | 6.0 |
| Evaluation | Smoothness of hair during foaming | A | B | B | A | B | C | C | B | C | B |
|  | Softness of hair during foaming | A | A | A | B | C | C | C | C | C | B |
|  | Smoothness of hair during rinsing | A | A | A | B | B | B | B | C | D | D |
|  | Smoothness of hair after drying | A | A | A | A | C | C | C | C | B | C |

*silicone derivative:

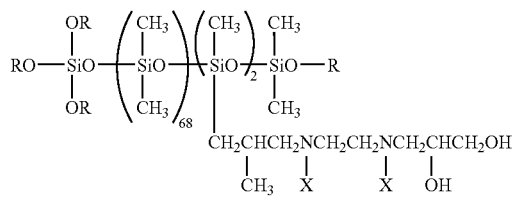

R: $C_{13}H_{27}$ to $C_{15}H_{31}$

X: 75% of —$CH_2CH(OH)CH_2OH$, 25% of hydrogen atom

Example 5

Conditioning Shampoo

|  | (wt. %) |
|---|---|
| Sodium polyoxyethylene (2) lauryl ether sulfate | 11.0 |
| Cationized cellulose *1 | 0.4 |
| Silicone derivative *2 | 1.0 |
| Dimethylpolysiloxane (viscosity: 100,000 mPa · s) | 0.5 |
| Cocamidopropyl betaine | 3.0 |
| Cocamide MEA | 0.5 |
| Ethylene glycol distearyl ester | 1.0 |
| Sodium chloride | 0.5 |
| Perfume | trace |
| Citric acid | q.s. |
| Purified water | Balance |

*1 "UCare Polymer JR-30M", product of Amerchol, $M_w$: 900,000, charge density: 1.2 meq/g)
*2 sold from Dow Corning under the name of "8500 CONDITIONING AGENT". It contains, as an effective ingredient, 60 wt. % of a silicone derivative (CAS No. 237753-63-8) having a group containing both a hydroxy group and a nitrogen atom as a side chain.

It has been found that the shampoo thus obtained (having pH of 6.0 when diluted to 20 times the weight) was excellent in smoothness and softness of the hair during the period of time from foaming to rinsing, and smoothness after drying.

Example 6

Conditioning Shampoo

|  | (wt. %) |
|---|---|
| Sodium polyoxyethylene (2) lauryl ether sulfate | 10.0 |
| Sodium lauryl sulfate | 5.0 |
| Cationized cellulose *1 | 0.7 |
| Silicone derivative *2 | 0.5 |
| Cocamide MEA | 1.0 |
| Myristyl alcohol | 1.0 |
| Cetanol | 0.5 |
| Behenyl trimonium chloride | 0.3 |
| Ethylene glycol distearyl ester | 1.0 |
| Glycerin | 1.0 |
| Sodium chloride | 1.0 |
| Perfume | trace |

-continued

|  | (wt. %) |
|---|---|
| Citric acid | q.s. |
| Purified water | Balance |

*1 "UCare Polymer JR-30M", product of Amerchol, $M_w$: 900,000, charge density: 1.2 meq/g)
*2 sold from Dow Corning under the name of "8500 CONDITIONING AGENT". It contains, as an effective ingredient, 60 wt. % of a silicone derivative (CAS No. 237753-63-8) having a group containing both a hydroxy group and a nitrogen atom as a side chain.

It has been found that the shampoo thus obtained (having a pH of 3.7 when diluted to 20 times the weight) was excellent in smoothness and softness during the period of time from foaming to rinsing, and smoothness after drying.

The invention claimed is:

1. A detergent composition comprising the following components (a), (b) and (c):
    (a) an anionic surfactant,
    (b) a water soluble cationized polymer having a weight average molecular weight of from 100,000 to 2,000,000 and a charge density of from 0.6 to 4 meq/g, and
    (c) a silicone derivative having a group containing both a hydroxy group and a nitrogen atom as a side chain thereof bonded to a silicon atom.

2. The detergent composition of claim 1, wherein the weight ratio of Component (b) and Component (c), (b)/(c), falls within a range of from 1/10 to 10.

3. The detergent composition of claim 1, wherein the anionic surfactant as Component (a) is selected from the group consisting of alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkylphenyl ether sulfates, higher fatty acid salts, and mixtures thereof.

4. The detergent composition of claim 1, wherein the polymer as Component (b) has a weight average molecular weight of from 300,000 to 1,800,000 and has a charge density of from 0.6 to 3 meq/g.

5. The detergent composition of claim 1, wherein the polymer as Component (b) is selected from the group consisting of cationized cellulose derivatives, cationic starch, cationized guar gum derivatives, homopolymers of diallyl quaternary ammonium salts, diallyl quaternary ammonium salt/acrylamide copolymers, quaternized polyvinylpyrrolidone derivatives, polyglycol polyamine condensates, vinylimidazolium trichloride/vinylpyrrolidone copolymers, hydroxyethyl cellulose/dimethyldiallylammonium chloride copolymers, vinylpyrrolidone/quaternized dimethylaminoethyl methacrylate copolymers, polyvinylpyrrolidone/alkylamino acrylate copolymers, polyvinylpyrrolidone/alkylamino acrylate/vinylcaprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, adipic acid/dimethylaminohydroxypropyl ethylenetriamine copolymer, and mixtures thereof.

6. The detergent composition of claim 1, wherein the silicone derivative as Component (c) is represented by the following average formula (1) below:

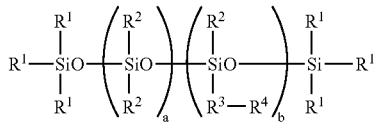
(1)

wherein, $R^1$s each independently represents a monovalent hydrocarbon group, a hydroxy group or an alkoxy group, $R^2$ each independently represents a monovalent hydrocarbon group, $R^3$ each independently represents a divalent $C_{1-10}$ hydrocarbon group, $R^4$ each independently represents a group represented by the following formula (2) or (3):

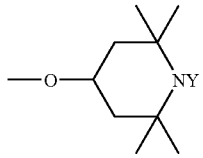
(2)

(3)

wherein, Y each independently represents a hydrogen atom or a group: —$CH_2CH(OH)$—$R^3$—$OH$ ($R^3$ has the same meaning as described above), $R^5$ each independently represents a hydrogen atom or a group —$R^3NY_2$ (Y and $R^3$ have the same meanings as described above), with the proviso that all the Ys do not represent a hydrogen atom simultaneously, a stands for a number of from 25 to 1,000, and b stands for a number of from 1 to 200.

7. The detergent composition of claim 2, wherein the ratio is from ⅕ to 5.

8. A detergent composition comprising the following components (a), (b) and (c):
   (a) from 0.5% to 60 wt. % of an anionic surfactant,
   (b) from 0.01% to 3 wt. % of a water soluble cationized polymer having a weight average molecular weight of from 100,000 to 2,000,000 and a charge density of from 0.6 to 4 meq/g, and
   (c) from 0.05% to 4 wt. % of a silicone derivative having a group containing both a hydroxy group and a nitrogen atom as a side chain thereof bonded to a silicon atom.

* * * * *